United States Patent [19]

Douglas et al.

[11] 4,203,984

[45] May 20, 1980

[54] ANTISECRETORY TRIAZINONES

[75] Inventors: George H. Douglas, Malvern; Ghulam N. Mir, Buckingham; Chong M. Won, Warrington; William L. Studt, Harleysville, all of Pa.

[73] Assignee: William H. Rorer, Inc., Fort Washington, Pa.

[21] Appl. No.: 959,950

[22] Filed: Nov. 13, 1978

[51] Int. Cl.$^2$ .................... A61K 31/53; A61K 31/54; A61K 31/535

[52] U.S. Cl. .................................. 424/249; 424/246; 424/248.5; 424/248.54

[58] Field of Search .......................................... 424/249

[56] References Cited

U.S. PATENT DOCUMENTS 3,966,728  6/1976  Murai et al. ..................... 424/249

Primary Examiner—Frederick E. Waddell
Attorney, Agent, or Firm—Ernest G. Szoke

[57] ABSTRACT

1,4-disubstituted-1,2-dihydro-1,3,5-triazine-2-ones and their pharmaceutically acceptable salts are used in the prevention and treatment of gastrointestinal disorders associated with hyperactivity of the secretory glands in the gastrointestinal tract.

9 Claims, No Drawings

ANTISECRETORY TRIAZINONES

BACKGROUND OF THE INVENTION

The present invention pertains to the treatment of gastrointestinal disorders caused by or accompanied by excessive gastric secretion. In accordance with the treatment provided, escessive gastric secretions are suppressed without any detectable side effects.

A variety of gastrointestinal disorders and discomfort including gastritis and peptic ulcers are associated with increased gastric acid secretion and/or increased gastric acidity. The most frequently employed therapeutic treatment for such conditions involves dietary therapy and regular use of antacids. Methods to reduce gastric secretion directly without other side effects are not generally known. In general, drugs which are known to reduce secretion in the G.I. tract at dosage levels needed to obtain a significant antisecretory effect, also produce undesirable side effects so that the drug cannot be administered for prolonged periods without causing other problems resulting from the side effects or causing patient discomfort resulting in patient resistance to taking the drug.

It is generally acknowledged that reduction of gastric secretion and total acidity are beneficial in the management of peptic ulcers, and surgical procedures are available for reducing gastric secretion. However, to avoid such radical non-reversible procedure, it is desired to provide therapeutic agents having significant antisecretory effects without accompanying side effects, that is, drugs having a therapeutic index which enables their use to achieve significant reduction in gastric secretion without adverse side effect. In accordance with the present invention, it has been found that certain 1,4-disubstituted-1,2-dihydro-1,3,5-triazin-2-ones when administered orally, produce significant reduction in gastrointestinal secretion at dosage levels at which there are not detectable effects ordinarily encountered in using known drugs for suppression of gastric secretion.

SUMMARY OF THE INVENTION

This invention pertains to a novel method for reducing gastric acid secretions thereby to prevent conditions caused by hypersecretion, and also involves a novel method for the treatment of gastrointestinal disorders brought about by excessive activity of the secretory glands of the stomach and intestines. The treatment may be used alone or in conjunction with recognized methods for control of hypersecretions in the gastrointestinal tract including dietary therapy and antacid treatment.

DETAILED DESCRIPTION OF THE INVENTION

The present invention involves the treatment of animal or human patients suffering the effects of hyperactivity of the secretory glands of the stomach or intestines by administering an effective antisecretory amount of a compound of the formula:

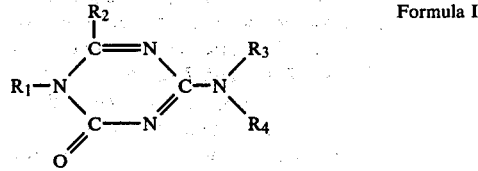

Formula I wherein $R_1$ is phenyl, benzyl or phenethyl; or phenyl, benzyl or phenthyl in which one or more of the phenyl hydrogens are substituted by lower alkyl, lower alkoxy, halo, halo-lower alkyl, amino, nitro, acyloxy, acylamino, hydroxy, cyano, carboxyl or lower alkyl sulfonyl, pyridyl or substituted pyridyl; $R_2$ is hydrogen or lower alkyl, and $R_3$ and $R_4$ are each independently selected from the group consisting of hydrogen, hydroxyl, lower alkanoyl, lower alkyl, lower alkenyl, lower alkynyl, lower alkoxy, halo lower alkyl, hydroxy lower alkyl, lower alkoxy lower alkyl, phenoxy lower alkyl, di-lower alkyl-amino lower alkyl or $R_3$ and $R_4$ together with the nitrogen to which they are attached form a 5 or 6 membered nitrogen heterocycle containing 0 to 1 additional hetero atoms which may be nitrogen, oxygen or sulfur; and their non-toxic salts.

As used herein, the term "lower alkyl" means a saturated or branched chain hydrocarbon containing from 1 to 6 carbon atoms such as methyl, ethyl, propyl, isopropyl, butyl, secondary butyl, tertiary butyl, isopentyl and the like. The term "substituted phenyl" is intended to include phenyl groups in which one or more of the hydrogen atoms has been replaced by a lower alkyl, hydroxy, nitro, amino, halo-lower alkyl, acyl, acylamino, lower alkoxy, cyano or lower alkyl sulphonyl. The term "substituted pyridyl" means a pyridyl group having one or more hydrogens replaced by lower alkyl, hydroxyl, nitro, amino, halo-lower alkyl, acyl, acylamino, lower alkoxy, cyano, carboxyl, or lower alkyl sulfonyl as in the case of substituted phenyl as defined above.

The term "halo" is intended to include all four halogens; i.e. chloro, bromo, iodo and fluoro, with chloro and fluoro being particularly preferred. The term "acyl" as used herein means an organic acid radical such as carboxyl, acetoxy, propionoxy, etc.

A particularly preferred group of 1,4-disubstituted-1,2-dihydro-1,3,5-triazin-2-ones useful in this invention are the compounds of the formula:

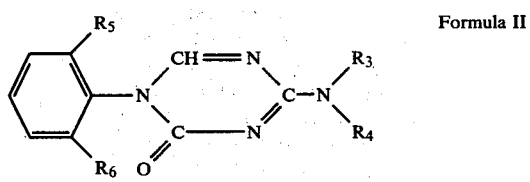

Formula II wherein $R_3$ and $R_4$ are independently selected from the group consisting of hydrogen, lower alkyl, hydroxyl, or lower alkoxy and $R_5$ and $R_6$ are each independently selected from the group consisting of hydrogen, halo, lower alkyl, lower alkoxy, or halo lower alkyl; and the non-toxic salts thereof.

A still more preferred group are the compounds of formula II above wherein $R_3$ is hydrogen; $R_4$ is lower alkyl or lower alkoxy; and $R_5$ and $R_6$ are the same and are each lower alkyl or lower alkoxy.

The preparations of these compounds are described in an application filed simultaneously herewith and assigned to applicant's assignee. Said copending application is entitled "Triazinones" and the applicants are Douglas, Studt, Won and Dodson Ser. No. 959,611, filed Nov. 13, 1978. For a more complete description of the triazine derivatives, their synthesis and properties, reference may be had to such copending application the disclosure of which is incorporated herein by reference.

The compounds of Formula I above can be used therapeutically in the treatment of conditions such as acute or chronic ulcers of the stomach and duodenum. These compounds are useful in suppressing the secretion of acid gastric juices and are beneficial in preventing and relieving symptoms of gastrointestinal distress associated with hypersecretion. They are also useful in preventing recurrence of conditions such as gastric ulcers in which hypersecretion of acid juices is regarded as a significant causative factor.

Pharmacological tests in animals which are generally recognized as models for determining antisecretory activity in humans, have shown that the compounds of the above structure when administered orally, provide useful antisecretory effects at dose levels which are well tolerated and for which no significant side effects have been observed. Particularly, these compounds produce antisecretory effects without affecting the cardiovascular system or the central nervous system, and with no conventional local anesthetic effect. Compounds which are effective in suppressing secretory action in the gastrointestinal tract without any central nervous system, cardiovascular or local anesthetic effects are not generally available. Accordingly, the above compounds when formulated into therapeutic dosage forms provide a beneficial means for the treatment of gastrointestinal disorders associated with excessive or abnormal activity of the gastrointestinal secretory glands.

The compositions of the present invention can be prepared in forms suitable for administration to humans and animals by compounding an effective single dose amount of a compound of formula I above with known ingredients generally employed in the preparation of therapeutic compositions provided as tablets, capsules, lozenges, chewable lozenges, pill, powder, granules, suspension, oil-in-water or water-in-oil emulsions, or other similar forms which can be taken orally. Since the compounds are readily absorbed into the blood stream from the stomach and intestines when taken orally, the preferred method of treatment is to give the drug orally which is also the safest and most practical route of administration. Optional methods can be used. Where, for example, the patient cannot swallow or has difficulty in swallowing, other methods of administration which permit the drug to be absorbed from the gastrointestinal tract or which deliver a solution of the drug directly to the blood stream can be employed.

In general, compounds of formula I above are indicated for use as pharmacotherapeutic agents in a wide variety of mammalian conditions which require suppression of gastrointestinal secretion either remedially or prophylactically or in combination with other therapy including treatments which cause excessive or unusual secretory activity as an undesired side effect.

The dosage regimens in carrying out the pharmacotherapeutic methods utilizing the triazine compositions of this invention are those which insure maximum therapeutic response until improvement is obtained and thereafter the minimum effective level which gives relief. Thus, in general, the dosages are those that are therapeutically effective in the treatment of diarrhea. In general, the single oral dose will contain between about 1 mg. and 100 mg (preferably in the range of 10 to 50 mg.) Fractional or multiple doses can of course be given bearing in mind that in selecting the appropriate dosage in any specific case, consideration must be given to the patient's weight, general health, age, and other factors which may influence response to the drug. The drug response on oral administration usually follows within 10 to 30 minutes after administration and is maintained for 1 to 4 hours. The drug is generally given in single doses 2 to 6 times daily or as required to maintain an effective drug level in the blood stream for continuous suppression of secretory action. In general, effective levels can be maintained by administering about 15 to 25 mg. per kg of body weight every 4 to 6 hours. The dose level varies with other routes of administration such as parenteral or anal. Alternatively, the drug can be administered for formulations which provide sustained release at active levels. The antisecretory effect is dose related through a minimum dose of about 10 to 15 mg/kg is ordinarily required to produce a detectable effect and the maximum effect is usually achieved at doses well below the maximum tolerated dose.

Compositions intended for oral use may be prepared according to methods known generally in the art, such compositions may contain one or more agents selected from the group consisting of sweetening agents, flavoring agents, coloring agents and preserving agents, in order to provide a pharmaceutically elegant and palatable preparation. Orally, they may be administered in tablets, lozenges, aqueous or oily suspensions, dispersible powders or granules, emulsion, hard or soft capsules, or syrups or elixers which contain the active triazine ingredient in admixture with non-toxic pharmaceutically acceptable excipients. Excipients which may be, for example, inert diluents, such as calcium carbonate, sodium carbonate, lactose, calcium phosphate or sodium phosphate; granulating and disintegrating agents, for example, starch, gelatin, or acacia; and lubricating agents, for example, magnesium stearate, stearic acid or talc. The tablets may be uncoated or they may be coated by known techniques to make them more effective for example to delay disintegration or absorption or to make them more palatable or for other reasons for which orally administered drugs have been previously provided in coated form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid paraffin or olive oil.

Aqueous solutions containing the active triazine form a further embodiment of this invention. Excipients suitable for aqueous suspensions, may be employed if desired. These excipients are suspending agents, for example, sodium carboxymethyl-cellulose, methyl-cellulose, hydroxypropylmethylcellulose, sodium alginate, polyvinylpyrrolidine, gum tragacanth and gum acacia; dispersing or wetting agents may be a naturally occurring phosphatide, for example, lecithin; or condensation products or an alkylene oxide with fatty acids, for example, polyoxyethylene stearate; or condensation products of ethylene oxide with long-chain aliphatic alcohols, for example, heptadecaethyleneoxy-cetanol; or condensation products of ethylene oxide with partial esters derived from fatty acids and a hexitol, for example, polyoxyethylene sorbitol mono-oleate; or condensation products of ethylene oxide with partial esters derived from fatty acids and hexitol anhydrides, for example, polyoxyethylene sorbitan mono-oleate. The said aqueous suspensions may also contain one or more preservatives, for example, ethyl, or n-propyl, p-hydroxy benzoate, one or more coloring agents, one or more flavoring agents, and one or more sweetening agents, such as sucrose.

Oily suspensions may be formulated by suspending the active ingredient in a vegetable oil, for example, arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents, may also be present.

The compounds of this invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleate. The emulsions may also contain sweeping and flavoring agents.

Syrups and elixirs may be formulated with sweetening agents, for example, glycerol, sorbitol or sucrose. Such formulations may also contain a demulcent, a preservative and flavoring and coloring agents. The pharmaceutical compositions may be in the form of a sterile injectionable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a nontoxic parenterally-acceptable diluent or solvent, for example, as an aqueous solution buffered to a pH of 4.0 to 7.0 and made isotonic with sodium chloride.

Further, the active triazine may be administered alone or in admixture with other agents having the same or different pharmacological properties.

Generally, these compounds may be tableted or otherwise formulated for oral use so that for every 100 parts by weight of the composition, there are present between 5 and 95 parts by weight of the active ingredient.

Various tests carried out in animal models show that triazinones of formula I above exhibit reactions that can be correlated with antisecretory activity in humans. The following tests show the ability of these compounds to inhibit gastrointestinal secretions in test animals indicative of antisecretory activity in humans. These are considered to be standard tests used to determine antisecretory properties. This correlation can be shown by the activities of compounds known to be clinically active and particularly previous experience in animals and humans with corresponding amidinoureas.

The test compound is dissolved in distilled water, unless otherwise stated.

INHIBITION OF GASTRIC ACID SECRETION IN THE RAT

The method used has been reported by Shay. Male Sprague-Dawley rats (140-160 g) were fasted 24 hours prior to the test. The rats were allowed water ad libitum only during the fasting period. One hour before pyloric ligation, the rats (5/group) were given either 1-(2'6'-dimethylphenyl)-4-methylamino-1,2-dihydro-1,3,5-triazin-2-one hydrochloride, atropine sulfate or the vehicle. The compounds were prepared in methylcellulose. Pyloric ligation was performed in the rats under sodium methohexital anesthesia. Four hours after pyloric ligation the rats were sacrificed by cervical dislocation, the stomachs were removed and the gastric contents were assayed for volume, titratable acidity and tirratable acid output (TAO). A 1 ml. aliquot of the gastric contents was titrated with 0.1 N naOH to pH 7.0 for titratable acidity. The percent of inhibition was calculated according to the formula:

(Mean control−mean treated)/Mean control×100

The antisecretory effects of compounds of Formula I is shown by the results with a representative triazinone. 1-(2'6'-dimethylphenyl)-4-methylamino-1,2-dihydro-1,3,5-triazin-2-one hydrochloride inhibited gastric acid secretion in the Shay rat as follows: Oral dose mg/kg 20; No. of rats, 5; Volume 81; Concentration 78; Total Acid Output 96. In contrast to atropine, a specific anticholonergic drug which caused mydriasis at doses as low as 2 mg/kg, 1-(2'6'-dimethylphenyl)-4-methylamino-1,2-dihydro-1,3,5-triazin-2-one hydrochloride was devoid of the mydriatic effect at 20 and 16 mg/kg, respectively.

The following examples are given by way of illustrating the preparation of the active triazinones used in the method and compositions of this invention. Novel therapeutic compositions are also exemplified. It will be understood that variations in amounts and adjuvants used in compounding suitable compositions can be made without departing from the teaching of this invention which is the administration of a 1,4-disubstituted-1,2-dihydro-1,3,5-triazin-2-ome of formula I in a manner and in amounts sufficient to provide and maintain an effective level in the G.I. tract for either prophylactic or therapeutic suppression of excessive secretory gland activity. If desired, the compounds can be formulated with other active ingredients or administered with other drugs or as part of a program of therapy that includes suppression of gastrointestinal secretion. The salts of compounds of formula I including acid addition salts and quarternary ammonium salts are particularly suitable for preparing pharmaceutical compositions. The acid addition salts of strong acids such as the hydrochloride, the hydrobromide, sulfate, nitrate, phosphate, methane sulfonate, benzene sulfonate and the like are especially useful. The salts of any strong Lewis acids can be used.

EXAMPLE 1

Preparation of
1-(2',6'-dimethylphenyl)-4-methylamino-1,2-dihydro-1,3,5-triazin-2-one About 200 mg of 1-(2,6-dimethylphenyl)-3-methylamidinourea hydrochloride was introduced in a gas chromatograph hypo vial and dissolved in 1 ml of acetonitrile. To the solution was added 0.2 ml of DMF DMA reagent. The vial was sealed with crimper and heated at 105° C. for 15 minutes in an oven. Seven vials were made. The contents of the vials were then put into a long-neck round bottom flask and evaporated to dryness by a flask evaporator. The solid mass was dissolved in a mixture of 30 ml of $CHCl_3$ and 20 ml of water and shaken vigorously in a 60 ml separatory funnel. The aqueous layer was discarded and 20 ml of water was added and shaken. The $CHCl_3$ layer was then taken and about 10 g of anhydrous $Na_2SO_4$ was added, the $CHCl_3$ solution was decanted into a flask and evaporated to dryness. The solid material was dissolved in pentanone-2 (about 80 ml) at 70° C. The solution was concentrated and crystallized upon cooling. The crystals were collected and dried in a desiccator with $P_2O_5$ with vacuum for one hour.

Elemental Analysis—MW: 230.26, MP: 225°–226° C.

|  | C | H | N |
|---|---|---|---|
| Calculated | 62.59 | 6.13 | 24.33 |
| Found | 62.84 | 6.15 | 24.28 |

EXAMPLE 2

Preparation of
1-(2',6'-diethylphenyl)-4-methylamino-1,2-dihydro-1,3,5-triazin-2-one The same procedure was followed as in Example 1 above using 1-(2,6-diethylphenyl)-3-methylamidinourea as the starting material and using as the recrystallization medium a mixed solvent of pentanone and hexane (30:10).

Elemental Analysis—MP:210°–211° C.

|  | C | H | N |
|---|---|---|---|
| Calculated | 65.09 | 7.02 | 21.89 |
| Found | 65.34 | 7.01 | 21.83 |

EXAMPLE 3

1-(2',6'-dimethylphenyl)-4-methylamino-1,2-dihydro-1,3,5-triazin-2-one-hydrochloride To a suspension of 10.0 g (30.0 m mole) of 1-(2,6-dimethylphenyl)-3-methylamidinourea hydrochloride in acetonitrile ($CH_3CN$) (50 ml) was added 9.3 g (78.0 m mol) of dimethylformamide dimethylacetal (DMF-DMA) and the resulting solution in a bomb was heated to 100°–105° C. for one hour. After cooling, the reaction mixture was placed in a round bottom flask and concentrated under reduced pressure. The residue was partitioned between $H_2O$ and $CHCl_3$ and the layers separated. The aqueous layer was extracted with $CHCl_3$ (1×50 ml). The combined $CHCl_3$ extracts were washed with $H_2O$ (1×50 ml) dried ($MgSO_4$) and concentrated under reduced pressure. A small amount of the residue was triturated in hexanes to give a white solid, having melting point 224° C., NMR and IR showed the product to be identical with that of Example 3. The remainder of the residue was dissolved in MeOH and acidified with HCl/MeOH. The MeOH was removed under vacuum and the residue crystallized from $CH_3CN$ to give 6.8 g (65%) of 1-(2,6-dimethylphenyl)-4-methylaminotriazin-2(6H)-one hydrochloride, melting point 234°–8° C. (decomposition).

Analysis calculated for: $C_{12}H_{15}ClN_4O$.

|  | C | H | N | CL |
|---|---|---|---|---|
| Calculated: | 54.04 | 5.67 | 21.01 | 13.29 |
| Found: | 54.14 | 5.80 | 21.90 | 13.28 |

EXAMPLE 4

1-(2',6'-dimethylphenyl)-4-methylamino-1,2-dihydro-1,3,5-triazin-2-one methanesulfonate A solution of 6.0 g (0.026 moles) of 1-(2,6-dimethylphenyl)-4-methylamino-dihydro-1,3,5-triazin-2-one in 100 ml iPA was prepared with warming. To the warm solution was added 2.0 ml (0.031 moles) of methane-sulfonic acid. The mixture became hot and crystals of white crystalline solid began to form almost immediately. The mixture allowed to cool to room temperature in tap water and filtered. The solution was washed with iPA/$Et_2O$ to give 8.00 g of product which was dried overnight at 50°–60° C. in a vacuum. Obtained 8.0 g of 1-(2,6-dimethylphenyl)-4-methylaminodihydro-1,3,5-triazin-2-one methanesulfonate after drying.

Calculated for: $C_{13}H_{18}N_4O_4S$—MW:326.35, MP:262°–65° C. dec.

|  | C | H | N | S |
|---|---|---|---|---|
| Calculated: | 47.84 | 5.57 | 17.17 | 9.80 |
| Found | 48.03 | 5.71 | 17.25 | 10.27 |

EXAMPLE 5

1-(2',6'-diethylphenyl)-4-methylamino-1,2-dihydro-1,3,5-triazin-2-one hydrochloride To a suspension of 22.8 g (80.0 mmol) of 1-(2,6-diethylphenyl)-3-methylamidinourea hydrochloride in $CH_3CN$ (100 ml) were added 19.1 g (160.0 mmol) of DMF-DMA and the reaction mixture was heated at reflux for 3 hours. The $CH_3CN$ was removed under reduced pressure and the residue partitioned between $CHCl_3$ and $H_2O$. The layers were separated and the aqueous layer extracted with $CHCl_3$ (1×100). The combined $CHCl_3$ extracts were washed with $H_2O$ (1×100 ml), dried ($MgSO_4$) and concentrated under reduced pressure to give an off-white solid, which by NMR confirmed the desired free base. The solution was dissolved in $H_2O$ and acidified with HCl/MeOH and the MeOH removed under reduced pressure to give an off-white solid which was crystallized from $CH_3CN$ to give after vacuum drying over the weekend (105° C., house vacuum) 16.7 g (71%) of crude product. The material was recrystallized from $CH_3CN$ (a hot filtration was necessary to remove some undissolved solid) to give 11.0 g (47%) of desired product as a white crystalline solid:

Analysis calculated for: $C_{14}H_{18}N_4OHCl$—MP:208°–15° C.

|  | C | H | N | Cl |
|---|---|---|---|---|
| Calculated: | 57.04 | 6.50 | 19.01 | 12.03 |
| Found: | 57.14 | 6.51 | 19.38 | 12.01 |

EXAMPLE 6

4-dimethylamino-1-(2',6'-dimethylphenyl)-1,2-dihydro-1,3,5-triazin-2-one hydrochloride To a suspension of 19.0 g (0.07 mole) of 1-(2,6-dimethylphenyl)-3-(N,N-dimethyl)-amidinourea in acrylonitrile (100 m) were added 16.7 g (0.14 mole) of DMF-DMA and the mixture refluxed for 2 hours. The acrylonitrile was removed under reduced pressure and the residue partitioned between $H_2O$ and $CHCl_3$. The layers were separated and the aqueous layer extracted with $CHCl_3$ (1×100 ml). The $CHCl_3$ extracts were washed with $H_2O$ (1×50 ml), dried over $MgSO_4$ and concentrated at reduced pressure to give an oil. Trituration of the oil in EtOH precipitated a white solid which was filtered and washed with EtOH to give the desired product after air drying. The solid was dissolved in MeOH and acidified with HCl/MeOH. The MeOH was removed under reduced pressure to give a white solid which was triturated with $CH_3CN$, filtered and washed with $CH_3CN$ to give 7.5 g (38%) of product which by NMR seemed to be a hydrate or wet. The solid was vacuum dried for 6 hours at 100° C. under vacuum.

Analysis calculated for: $C_{13}H_{10}N_4O \cdot HCl$.

|  | C | H | N | Cl |
|---|---|---|---|---|
| Calculated: | 55.61 | 6.10 | 19.96 | 12.63 |
| Found: | 55.81 | 5.96 | 20.31 | 12.46 |

EXAMPLE 7

Therapeutic compositions of the invention are prepared by using known techniques for compounding employing either the base or a salt as the active ingredient along with the non-toxic excipients chosen in accordance with the particular form and properties desired for the therapeutic composition.

Tablets which can be advantageously used to inhibit or suppress gastrointestinal secretions to prevent or treat conditions associated with excessive secretory action can be provided in a form which reduces the total secretion when taken at a rate of 4 to 6 tablets per day containing between about 200 to 1000 mg of the active ingredient. An exemplary formulation which can be utilized is, for example, the following.

1-(2'6'-dimethylphenyl)-4-methylamino-1,2-dihydro-1,3,5-triazin-2-one: 500 mg.
tricalcium phosphate: 200 mg.
talc: 50 mg.
magnesium stearate: 10 mg.
polyvinyl acetate: 40 mg.

In addition, there are added protective excipients such as ethylcellulose, dibutylphthalate, propylene glycol, wax (white and/or carbauba), spermaceti, methylene chloride, and rectified diethyl ether. The ingredients are compressed to minimum size to provide a tablet of about 850 mg.

EXAMPLE 8

A lot of 1,000 tablets each containing 1 g of 1-(2'6'-diethylphenyl)-4-methylamino-1,2-dihydro-1,3,5-triazin-2-one is prepared from the following types and amounts of ingredients:

1-(2'6'-diethylphenyl)-4-methylamino-1,2-dihydro-1,3,5-triazin-2-one: 1 kg.
dicalcium phosphate: 1 kg.
methylcellulose USP: 75 g.
talc: 150 g.
cornstarch: 200 g.
magnesium stearate: 10 g.

The active ingredient and diacalcium phosphate are mixed thoroughly and granulated with a 7.5% solution of methyl-cellulose in water and passed through a #8 screen and air-dried. The dried granules are passed through a #12 screen and combined with the talc, starch and magnesium stearate with thorough mixing after which the composition is compressed into tablets.

EXAMPLE 9

A lot of 2-piece hard gelatin capsules, each containing 500 mg. of 1-(2',6'-dimethylphenyl)-4-methylamino-1,2-dihydro-1,3,5-triazin-2-one are prepared from the following types and amounts of ingredients (the amounts given are per capsule):

1-(2'6'-dimethylphenyl)-4-methylamino-1,2-dihydro-1,3,5-triazin-2-one: 500 g
dicalcium phosphate: 500 g.
talc: 150 g.
magnesium stearate: 5 g.

The ingredients are mixed thoroughly and filled into capsules which are used for oral administration at the rate of about one every four hours. If desired, slow release forms can be provided or delay release forms depending on choice of capsules and formulating ingredients.

EXAMPLE 10

A sterile solution suitable for intramuscular or interperitoneal injection, and containing 10 mg. of 1-(2'6'-dimethylphenyl)-4-methylamino-1,2-dihydro-1,3,5-triazin-2-one hydrochloride in each, 10 ml. (1:1 wt./volume), is prepared from the following ingredients:

1-(2'6'-dimethylphenyl)-4-methylamino-1,2-dihydro-1,3,5-triazin-2-one hydrochloride: 10 g.
benzyl benzoate: 100 ml.
methylparaben: 1 g.
propylparaben-0.5 g.
cottonseed oil q.s.: 500 ml.

EXAMPLE 11

Ten thousand tablets for oral use, each containing 50 mg. of 1-(2'6'-dimethylphenyl)-4-methylamino-1,2-dihydro-1,3,5-triazin-2-one, are prepared from the following types and amounts of material:

1-(2'6'-dimethylphenyl)-4-methylamino-1,2-dihydro-1,3,5-triazin-2-one: 500 g.
Lactose U.S.P.: 350 g.
Potato Starch U.S.P.: 346 g.

The mixture is moistened with an alcoholic solution of 20 g. of stearic acid and granulated through a sieve. After drying, the following ingredients are added:
Potato Starch U.S.P.: 320 g.
Talc: 400 g.
Magnesium stearate: 500 g.
Colloidal silicium dioxide: 64 g.

The mixture is thoroughly mixed and compressed into tablets.

EXAMPLE 12

Five hundred ampoules each with two ml. of solution which contain 15 mg. of 1-(2'6'-dimethylphenyl)-4-methylamino-1,2-dihydro-1,3,5-triazin-2-one is prepared from the following types and amounts of materials:

1-(2'6'-dimethylphenyl)-4-methylamino-1,2-dihydro-1,3,5-triazin-2-one: 7.5 g.
Ascorbic acid: 1 g.
Sodium bisulphite: 0.5 g.
Sodium sulphite: 1 g.

EXAMPLE 13

Capsules are prepared as follows:
15 g. of 1-(2'6'-dimethylphenyl)-4-methylamino-1,2-dihydro-1,3,5-triazin-2-one,
3 g. magnesium stearate,
2 g. of finely divided silica sold under the trademark CAB-O-SIL by Godfrey L. Cabot, Inc., Boston, MA, and
369 g. of lactose.

The ingredients are thoroughly mixed with each other and the mixture is filled in gelatin capsules. Each capsule contains 500 mg. of the composition and thus, 15 mg. of 1-(2'6'-dimethylphenyl)-4-methylamino-1,2-dihydro-1,3,5-triazine-2-one.

EXAMPLE 14

50 g. of 1-(2'6'-dimethylphenyl)-4-methylamino-1,2-dihydro-1,3,5-triazin-2-one, 5 g. of propyl p-hydroxybenzoate are dissolved and dilluted to 5000 cc. with twice distilled water after the addition of modified Sorensen buffer solution in an amount sufficient to adjust the pH-value to a pH of 6.0. Sodium chloride is dissolved therein in an amount sufficient to render the resulting solution isotonic. The final solution is passed through a bacteriological filter and the filtrate is autoclaved at 120° C. for 15 minutes to yield a parenterally applicable solution which contains 50 mg. of 1-(2'6'-dimethylphenyl)-4-aminomethyl-1,2-dihydro-1,3,5-triazin-2-one in 5 cc.

EXAMPLE 15

By analogous procedures, other 1,4-disubstituted-1,2-dihydro-1,3,5-triazin-2-ones can be prepared from the corresponding amidinourea starting materials, and formulated for either oral administration, as injectable or infusible solutions or for rectal administration for example, suppository form.

Illustrative compounds which can be used as active ingredients in the therapeutic compositions of this invention prepared and formulated in accordance with the methods described herein, are the following:

1-(2'6'-diethylphenyl)-4-methylamino-1,2-dihydro-1,3,5-triazine-2-one
1-(2'6'-dimethylphenyl)-4-methylamino-1,2-dihydro-1,3,5-triazin-2-one-hydrochloride
1-(2'6'-dimethylphenyl)-4-methylamino-1,2-dihydro-1,3,5-triazin-2-one methanesulfonate
1-(2'6'-diethylphenyl)-4-methylamino-1,2-dihydro-1,3,5-triazin-2-one hydrochloride
4-dimethylamino-1-(2'6'-dimethylphenyl)-1,2-dihydro-1,3,5-triazin-2-one hydrochloride
1-(2-chloro-6-methylphenyl)-4-methylamino-1,2-dihydro-1,3,5-triazin-2-one
1-(2'6'-dimethylphenyl)-4-n-butoxyamino-1,2-dihydro-1,3,5-triazin-2-one
1-(2'6'-dimethylphenyl)-4-sec-butoxyamino-1,2-dihydro-1,3,5-triazin-2-one
4-methylamino-1-phenyl-1,2-dihydro-1,3,5-triazin-2-one-hydrochloride
1-(2-methylphenyl)-4-ethylamino-1,2-dihydro-1,3,5-triazin-2-one
1-(2'6'-dichlorophenyl)-4-methylamino-1,2-dihydro-1,3,5-triazin-2-one
1-(2-methylphenyl)-4-methylamino-1,2-dihydro-1,3,5-triazin-2-one
1-(2'6'-dimethylphenyl)-4-(2,2,2-trifluoroethylamino)-1,2-dihydro-1,3,5-triazin-2-one
1-(2-bromo-6-methylphenyl)-4-methylamino-1,2-dihydro-1,3,5-triazin-2-one
1-(2'6'-dimethylphenyl)-4-methoxyamino-1,2-dihydro-1,3,5-triazin-2-one hydrate
1-(2'6'-diethylphenyl)-4-propylamino-1,2-dihydro-1,3,5-triazin-2-one
1-(2'6'-diethylphenyl)-4-i-propylamino-1,2-dihydro-1,3,5-triazin-2-one
1-(2'6'-diethylphenyl)-4-propargylamino-1,2-dihydro-1,3,5-triazin-2-one
1-(2'6'-diethylphenyl)-4-cyclopropylamino-1,2-dihydro-1,3,5-triazin-2-one
1-(2'6'-diethylphenyl)-4-(N-pyrrolidinyl)-1,2-dihydro-1,3,5-triazin-2-one
1-(2'6'-diethylphenyl)-4-(N-piperidyl)-1,2-dihydro-1,3,5-triazin-2-one
1-(2'-methyl-6'-ethyl-phenyl)-4-methylamino-1,2-dihydro-1,3,5-triazin-2-one
1-(2'-methyl-6'-ethyl-phenyl)-4-(N,N-dimethylamino)-1,2-dihydro-1,3,5-triazin-2-one
1-(2'-methyl-6'-chlorophenyl)-4-methylamino-1,2-dihydro-1,3,5-triazin-2-one
1-(2'-methyl-6'-ethylphenyl)-4-(N-morpholinyl)-1,2-dihydro-1,3,5-triazin-2-one
1-(2'-methyl-6'-chlorophenyl)-4-(N-piperidinyl)-1,2-dihydro-1,3,5-triazin-2-one
1-(2'6'-dimethylphenyl)-4-[N-(3-thiomorpholinyl)]-1,2-dihydro-1,3,5-triazin-2-one
1-(2'6'-dimethylphenyl)-4-[N-(thioazolinyl)]-1,2-dihydro-1,3,5-triazin-2-one
1-(2'-chloro-6'-bromophenyl)-4-methylamino-1,2-dihydro-1,3,5-triazin-2-one
1-(2'6'-dichlorophenyl)-4-amino-1,2-dihydro-1,3,5-triazin-2-one
1-(2'-pyridyl)-4-methylamino-1,2-dihydro-1,3,5-triazin-2-one
1-(2'-pyridyl)-4-ethylamino-1,2-dihydro-1,3,5-triazin-2-one
1-(3'-ethyl-pyrid-2-yl)-4-ethylene-1,2-dihydro-1,3,5-triazin-2-one
1-(3'methyl-2-pyrid-2-yl)-4-methylamino-1,2-dihydro-1,3,5-triazin-2-one
1-(3'5'-dimethyl-pyrid-4-yl)-4-methylamino-1,2-dihydro-1,3,5-triazin-2-one
1-(2'4'-dimethyl-pyrid-3-yl)-4-methylamino-1,2-dihydro-1,3,5-triazin-2-one
1-(2'6'-dimethylbenzyl)-4-methylamino-1,2-dihydro-1,3,5-triazin-2-one
1-(2'6'-dimethylphenethyl)-4-methylamino-1,2-dihydro-1,3,5-triazin-2-one

We claim:

1. A method for inhibiting or suppressing the activity of the secretory glands in the gastrointestinal tract which comprises administering by oral or parenteral route to a patient suffering from hypersecretion an effective amount of an antisecretory composition consisting essentially of an inert pharmaceutical carrier and an effective antisecretory amount of a compound of the formula:

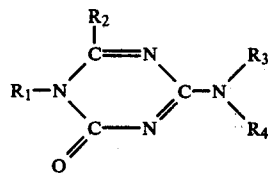

wherein $R_1$ is phenyl, benzyl or phenethyl; or phenyl, benzyl or phenethyl in which one or more of the phenyl hydrogens are substituted by lower alkyl, lower alkoxy, halo, halo lower alkyl, amino, nitro, hydroxy, cyano, carboxyl, or lower alkyl sulfonyl; pyridyl or pyridyl having one or more hydrogens replaced by lower alkyl, lower alkoxy, halo, halo lower alkyl, amino, nitro, hydroxy, cyano, carboxyl, or lower alkyl sulfonyl; $R_2$ is hydrogen or lower alkyl, and $R_3$ and $R_4$ are each independently selected from the group consisting of hydrogen, hydroxyl, lower alkanoyl, lower alkyl, lower alkenyl, lower alkynyl, lower alkoxy, halo lower alkyl, hydroxy lower alkyl, lower alkoxy lower alkyl, phenoxy lower alkyl, di-lower alkylamino lower alkyl; and their pharmaceutically acceptable salts.

2. A method according to claim 1 wherein the antisecretory compound is a compound of the formula:

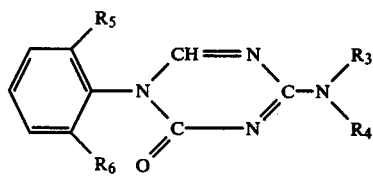

wherein $R_3$ and $R_4$ are independently selected from the group consisting of hydrogen, lower alkyl, hydroxyl and lower alkoxy and $R_5$ and $R_6$ are each independently selected from the group consisting of hydrogen, halo, lower alkyl, lower alkoxy or halo lower alkyl; and their pharmaceutically acceptable salts.

3. A method according to claim 2 wherein the antisecretory compound is a compound of the formula:

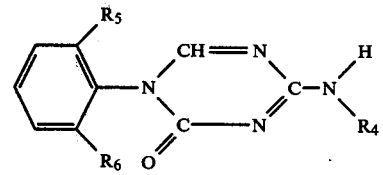

wherein $R_4$ is lower alkyl or lower alkoxy and $R_5$ and $R_6$ are each independently lower alkyl or lower alkoxy.

4. A method according to claim 3 wherein $R_5$ and $R_6$ are both the same and are both lower alkyl.

5. A method according to claim 4 wherein $R_4$ is lower alkyl.

6. A method according to claim 5 wherein each of $R_5$ and $R_6$ is methyl or ethyl.

7. A method according to any of claim 1 wherein the composition is in a dosage unit form suitable for oral administration.

8. A method according to claim 7 wherein the amount of antisecretory compound is between about 500 and about 1000 mg.

9. A method for inhibiting or suppressing the activity of the secretory glands in the gastrointestinal tract which comprises administering by oral or parenteral route to a patient suffering from hypersecretion, an effective amount of a compound of the formula:

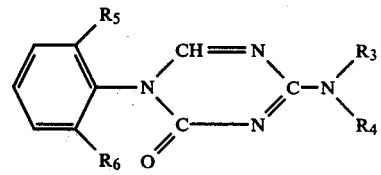

wherein $R_3$ and $R_4$ are independently selected from the group consisting of hydrogen, lower alkyl, hydroxyl and lower alkoxy or one of its pharmaceutical salts.

* * * * *